United States Patent [19]
Aubert et al.

[11] Patent Number: 5,858,928
[45] Date of Patent: Jan. 12, 1999

[54] GEL OF AN APOLAR MEDIUM, ITS USE FOR THE PREPARATION OF WATER-BASED DRILLING FLUIDS

[75] Inventors: Daniel Aubert, Thiais; Laurent Frouin, L'Hay Les Roses; Mikel Morvan, Courbevoie; Marie-Madeleine Vincent, Athis Mons, all of France

[73] Assignee: Rhone-Poulenc Chimie, Courbevoie, France

[21] Appl. No.: 561,725

[22] Filed: Nov. 22, 1995

[30] Foreign Application Priority Data

| Nov. 28, 1994 | [FR] | France | 94 14213 |
| May 19, 1995 | [FR] | France | 95 05963 |
| May 19, 1995 | [FR] | France | 95 05962 |
| Jul. 7, 1995 | [FR] | France | 95 08604 |

[51] Int. Cl.$^6$ .............. C09K 7/02; B01J 13/00
[52] U.S. Cl. .......... 507/128; 507/129; 507/132; 507/136; 507/140; 507/110; 507/235; 507/112; 507/113; 507/114; 507/119; 507/124; 507/123; 252/315.1
[58] Field of Search ........... 507/209, 213, 507/110, 215, 216, 235, 128, 140, 129, 132, 136; 252/315.1

[56] References Cited

U.S. PATENT DOCUMENTS

| 3,435,898 | 4/1969 | Thompson | 166/274 |
| 3,818,989 | 6/1974 | Christopher, Jr. et al. | 166/274 |
| 3,956,145 | 5/1976 | Christopher, Jr. et al. | 507/212 |
| 3,969,087 | 7/1976 | Saito et al. | 44/270 |
| 4,178,264 | 12/1979 | Streit et al. | 252/315.3 |
| 4,622,155 | 11/1986 | Harris et al. | 507/238 |
| 4,979,564 | 12/1990 | Kalpakci et al. | 166/273 |
| 5,034,139 | 7/1991 | Reid et al. | 252/8.512 |
| 5,082,059 | 1/1992 | Engelhardt et al. | 166/308 |
| 5,271,464 | 12/1993 | McCabe | 166/295 |
| 5,348,584 | 9/1994 | Brother et al. | 106/725 |
| 5,360,558 | 11/1994 | Pakulski et al. | 507/202 |
| 5,417,287 | 5/1995 | Smith et al. | 166/308 |
| 5,514,645 | 5/1996 | McCabe et al. | 507/238 |
| 5,571,315 | 11/1996 | Smith et al. | 106/285 |

FOREIGN PATENT DOCUMENTS

| 083 957 | 7/1983 | European Pat. Off. | B08B 9/04 |
| 1443654 | 7/1976 | United Kingdom . | |
| 084225 | 4/1982 | United Kingdom . | |

OTHER PUBLICATIONS

Seifen, Ole, Fette, Wachsen, vol. 116, No. 2, Feb. 1, 1990 Augsburg(DE).

Primary Examiner—Philip Tucker

[57] ABSTRACT

The invention relates to a gel made of apolar medium including:

an apolar medium, a "multichain" liquid surface-active agent in acidic form, soluble or dispersible in the said apolar medium, an agent for neutralizing the said "multichain" surface-active agent, from 0.2 to 5 molecules of water per molecule of "multichain" surface-active agent, optionally at least one emulsifying agent and/or a solid filler which is soluble or insoluble in the apolar medium.

This gel may be employed for the formulation of water-based drilling fluids.

26 Claims, 1 Drawing Sheet

GEL OF AN APOLAR MEDIUM, ITS USE FOR THE PREPARATION OF WATER-BASED DRILLING FLUIDS

BRIEF SUMMARY OF THE INVENTION

The present invention relates to a gel made of apolar medium which is relatively insensitive to temperature and capable of being employed as such in detergency for defatting textiles, as carrier for solid matter which sediments in ungelled apolar medium, in cosmetics etc., or, after dilution in an aqueous medium, as industrial cleaning agent for hard surfaces and especially for the formulation of water-based drilling fluids.

DETAILED DESCRIPTION OF THE INVENTION

According to the invention it is a gel characterized in that it contains:

at least one apolar medium (ApoM), at least one "multichain" liquid surface-active agent in acidic form (MCSA), which is soluble or dispersible in the said apolar medium, at least one agent for neutralizing (NA) the said "multichain" surface-active agent, present in a quantity corresponding to approximately 2 to 30 times, preferably 4 to 20 times the quantity necessary stoichiometrically for the neutralization of the said "multichain" surface-active agent in acidic form (MCSA), of the order of 0.2 to 5, preferably of the order of 0.3 to 3 molecules of water per molecule of "multichain" liquid surface-active agent in acidic form (MCSA), the water being introduced at least partly through the intermediacy of the said "multichain" surface-active agent in acidic form (MCSA) and/or through the intermediacy of the said neutralizing agent (NA), optionally at least one emulsifying agent capable of emulsifying the said gel in water or in an aqueous medium, and optionally at least one solid filler which is soluble or insoluble in the apolar medium (ApoM).

"Apolar medium" (ApoM) is intended to mean any constituent that is liquid at the temperature of preparation of the said gel, which, situated in the Hansen solubility space (Handbook of solubility parameters and other cohesion parameters, Allan F. M. Barton, CRC Press Inc., 1983) exhibits the following parameters:

$\delta P$ of Keesom interactions lower than 10 $(J/cm^3)^{1/2}$ $\delta H$ of hydrogen bonds lower than 10 $(J/cm^3)^{1/2}$ $\delta D$ of London interactions higher than 15 $(J/cm^3)^{1/2}$ By way of example of apolar medium (ApoM) there may be mentioned:

triglycerides of saturated or unsaturated fatty acids containing at least 12 carbon atoms and preferably from 14 to 20 carbon atoms; these are synthetic or preferably natural triglycerides such as the vegetable oils of the type of rapeseed oil, soya oil, groundnut oil, butter oil, cottonseed oil, linseed oil, coconut oil, olive oil, palm oil, grapeseed oil, fish oil, castor oil and coprah oil, aromatic petroleum cuts, terpenic compounds (D-limonene, L-limonene etc.), mixtures of dimethyl, dipropyl, diisobutyl, dibutyl, etc. succinate/adipate/glutarate diesters, aliphatic hydrocarbons containing at least 6 carbon atoms (isooctane, kerosene, petrol, diesel fuel, mineral oils, lubricating oils etc.), aromatic solvents (anisole, toluene etc.), chlorinated solvents (1,1,1-trichloroethane), and essential oils.

"Multichain" surfactant (MCSA) is intended to mean any liquid surfactant consisting of at least two hydrophobic chains connected through the intermediacy of a hydrophilic head, the said surfactant being in acidic form.

The surfactants based on the following may be mentioned by way of examples:

phosphate diesters of alkoxylated alcohols containing from 2 to 20, preferably from 4 to 10 oxyalkylene, preferably oxyethylene, units, and in the case of which the alcohols are chosen from $C_6$–$C_{30}$, preferably $C_6$–$C_{20}$ linear or branched, saturated or unsaturated aliphatic alcohols, phosphate diesters of alkoxylated alkylphenols containing from 2 to 20, preferably from 4 to 10, oxyalkylene, preferably oxyethylene, units, and in the case of which the alkylphenols are chosen from those in which the alkyl radical is $C_6$–$C_{30}$, preferably $C_6$–$C_{20}$.

The agents for neutralizing (NA) the said "multichain" surfactant (MCSA) are preferably liquid and insoluble in the said apolar suspension medium.

Among these there may be mentioned primary, secondary or tertiary amines, alkanolamines etc.

As examples there may be mentioned triethanolamine, aminomethylpropanol, cocoamine, butylamine etc.

As an example of agent capable of emulsifying the said gel of the invention in water or in an aqueous medium there may be mentioned ethoxylated tristyrylphenols, ethoxylated and/or propoxylated tristyrylphenol sulfates or phosphates, ethoxylated and/or propoxylated fatty acids or alcohols, ethoxylated/propoxylated block copolymers and sodium dodecylbenzenesulphonate.

The solid fillers which may be present may be inert fillers as well as chemically active fillers.

Examples which may be mentioned are especially:

fillers of the silica, calcium carbonate and pigment type, etc.

hydrocolloids capable of thickening aqueous media, such as:

polysaccharides obtained by bacterial fermentation (xanthan gum, polysuccinoglycans, rhamsan, welan, gellan etc.), galactomannans (guar gums and their derivatives, carob, tamarind, etc.), carrageenans, alginates, semisynthetic cellulose derivatives such as carboxymethyl celluloses, methyl celluloses, hydroxypropyl celluloses and hydroxyethyl celluloses, alkali metal polyacrylates, polyvinyl alcohols, polyethylene glycols, polyvinylpyrrolidones, by themselves or mixed with each other, foam suppressors such as aluminium stearate, hydrophobic silica, ethylenebisstearamide, etc.

active substances water-soluble basic compounds such as sodium metasilicates, clays, anti-UV agents such as titanium oxide, zinc oxide etc.

The viscoelastic characteristics of the gel are a function both of the molar ratio of neutralizing agent (NA)/ "multichain" surfactant (MCSA) and of the relative quantities of apolar medium (ApoM) and of "multichain" surfactant (MCSA).

The quantities of "multichain" surfactant (MCSA) are generally of the order of 0.5 to 10%, preferably of the order of 1 to 6% by weight relative to the weight of the said gel.

The gels forming the subject of the invention have the advantage of exhibiting viscoelastic characteristics which can range from those of the "flexible" (or "weak") gels to those of "hard" (or "strong") gels.

A gel is a viscoelastic system which can be characterized by a conservation modulus G' (expressing the solid nature of the gel) and a loss modulus G" (expressing the viscous nature) as a function of the angular rate of deformation.

A "hard" or ("strong") gel means any gel whose conservation modulus G' exhibits a plateau in a range of angular rate generally extending from $10^{-1}$ to 100 radians/s; in this range of angular rate G' is at least 4 times greater than G".

A "hard" (or "strong") gel can be favourably obtained with the aid of a quantity of "multichain" surfactant (MCSA) of the order of 5 to 10% by weight relative to the weight of the said gel, with a molar ratio of neutralizing agent (NA)/"multichain" surfactant (MCSA) of the order of 5 to 10 times the stoichiometric neutralization ratio and a quantity of water of the order of 0.05 to 0.5% by weight relative to the weight of the said gel.

A "flexible" (or "weak") gel means any gel whose conservation modulus G' exhibits a plateau in a range of angular rate lower than 1 radian/s and remains in this plateau higher than the loss modulus G".

Conditions which are favourable for obtaining a "flexible" (or "weak") gel correspond to the presence of a quantity of "multichain" surfactant (MCSA) of the order of 1 to 3% by weight relative to the weight of the said gel, with a molar ratio of neutralizing agent (NA)/"multichain" surfactant (MCSA) of the order of 5 to 10 times the stoichiometric neutralization ratio, and of a quantity of water of the order of 0.01 to 0.1% by weight relative to the weight of the said gel.

The gels forming the subject of the invention may have many applications, according to the nature of the apolar medium (ApoM) and the nature of the optional fillers.

The said gels may be employed as they are, for example:

in detergency, for the defatting of textiles by application of the said gel containing an active solvent for fats as apolar medium, to the surface to be treated as a carrier for suspending fillers which sediment naturally in an ungelled apolar medium, especially as a carrier for foam suppressors in cosmetics for the preparation of sun protection creams and gels containing anti-UV agents or for the preparation of care creams in which the continuous phase is an oil.

The gels according to the invention may also be employed, after dilution in an aqueous medium, as agents for industrial cleaning of hard surfaces.

Gels according to the invention which are particularly advantageous are those containing at least one solid filler chosen from hydrocolloids capable of thickening aqueous media, of the type of those mentioned above.

The invention therefore also relates to a specific gel (gel G1) usable particularly, after dilution in water, for the formulation of water-based drilling fluids and including:

100−(a+b+c+d) parts by weight of at least one apolar medium (ApoM), a quantity (a) of the order of 0.5 to 6, preferably of the order of 1 to 4 parts by weight of at least one "multichain" liquid surface-active agent in acidic form (MCSA), soluble or dispersible in the said apolar medium, a quantity (b) of at least one agent for neutralizing (NA) the said "multichain" surface active agent, corresponding to approximately 2 to 30 times, preferably 4 to 20 times the quantity which is stoichiometrically necessary for the neutralization of the said "multichain" surface-active agent in acidic form (MCSA), a quantity (c) of water corresponding to approximately 0.2 to 5, preferably approximately 0.3 to 3 molecules of water per molecule of "multichain" liquid surface-active agent in acidic form (MCSA), the water being introduced at least partially through the intermediacy of the said "multichain" surface-active agent in acidic form (MCSA) and/or through the intermediacy of the said neutralizing agent (NA), and a quantity (d) of the order of 10 to 50, preferably of the order of 20 to 40 parts by weight of at least one hydrocolloid capable of thickening aqueous media.

The hydrocolloids capable of thickening aqueous media may be chosen from the list defined above and in particular from xanthan gum, polysuccinoglycans, rhamsan, wellan and gellan.

According to a preferred embodiment of the invention, in the gel (gel G1), the hydrocolloid capable of thickening aqueous media is a mixture (M) containing:

at least one hydrocolloid polysaccharide obtained by bacterial fermentation (BPS), stable in the presence of $Ca^{2+}$ ions at a pH higher than 10 and exhibiting a pseudoplasticity value lower than or equal to 0.5 at a concentration of 0.1% by weight in distilled water and at least one hydrocolloid polymer of natural origin (NP), stable in the presence of cement and of $Ca^{2+}$ ions at a pH higher than 10 and exhibiting a pseudoplasticity value higher than or equal to 0.6 at a concentration of 0.3% by weight in distilled water according to an NP/BPS weight ratio of the order of 20/80 to 95/5, preferably of the order of 50/50 to 90/10.

The term "stable" in the presence of cement or of $Ca^{2+}$ ions at a pH higher than 10 means that the viscosity of an aqueous solution of the hydrocolloid is not affected by the presence of cement or by the presence of $Ca^{2+}$ ions at a pH higher than 10. For example, a hydrocolloid which, in aqueous solution at a concentration of 0.3% by weight, has a viscosity, at a given rate gradient, which does not vary by more than ±20%, preferably by not more than ±10% from its initial value, when 1% by weight, relative to the weight of the said solution, of a cement of Portland CPA 550 (marketed by Les Ciments Français) is added to it, may be considered to be stable.

The pseudoplasticity value mentioned is that calculated with the aid of the Ostwald model applied to the flow rheology curve obtained with the aid of a Low Shear apparatus marketed by Contraves.

This value is deduced from the following equation:

$$\log \eta = \log K + (n+1) \log \gamma$$

where η denotes the viscosity in mPa s, K the consistency value, n the pseudoplasticity value and γ the shear rate in $s^{-1}$.

Among the hydrocolloid polysaccharides obtained by bacterial fermentation (BPS) which may be present in the mixture (M) there may be mentioned:

succinoglycans in which the base unit contains glucose, galactose and a succinyl residue; these are described in European Patent Applications EP-A-351 303 and 40 445 and in Carbohydrate Research, 73 (1979) pp. 159–168, by Clarence A. Knutson; they can be obtained by microbial fermentation of a medium comprising a source of carbon, by means of a microorganism belonging to the genus Arthrobacter, such as *Arthrobacter stabilis,* in particular the strain *Arthrobacter stabilis* NRRL-B-1973, to the genus Agrobacterium, such as *Agrobacterium tumefaciens, Agrobacterium radiobacter* or *Agrobacterium rhizogenes,* to the genus Rhizobium, in particular *Rhizobium meliloti* and *Rhizobium trifoli,* to the genus Alcaligenes such as *Alcaligenes faecais,* in particular the variety myxogenes or to the genus Pseudomonas, in particular the strains Pseudomonas sp. NCIB 11264 and NCIB 11592; among these succinoglycans very particular mention may be made of the rheozan gums, described in European Patent Application EP-A-351 303 and obtained by fermentation of a carbonaceous source by means of the strain *Agrobacterium tumefaciens* 1–736 deposited at the National Collection of Culture of Microorganisms (NCCM);

rhamsan gums, in which the base unit contains glucose and rhamnose; these can be obtained by microbial fermentation of a medium comprising a source of carbon, by means of a microorganism belonging to the genus Alcaligenes, preferably the strain Alcaligenes ATCC 31961 or to the genus Pseudomonas, in particular the strains *Pseudomonas paucimobilis,* more preferably the strains 1–886 deposited at the NCCM and the strain DSM 4429; these polysaccharides are described in European Patent Applications EP-A-77 680 and 339 445;

welan gums in which the base unit contains glucose, glucuronic acid, rhamnose and mannose; these are described in P. E. Jansson, B. Lindberg and G. Wildmalm (1985) Carbohydrate Research 139, 217–223; they can be obtained by microbial fermentation of a medium comprising a source of carbon, by means of a microorganism belonging to the genus Alcaligenes preferably the strain Alcaligenes ATCC 31555.

Among the hydrocolloid polymers of natural origin (NP) there may be mentioned:

semisynthetic cellulose derivatives such as hydroxymethyl celluloses, hydroxyethyl celluloses, hydroxymethyl propyl celluloses, hydroxypropyl celluloses and carboxymethyl celluloses;

alkoxylated derivatives of guar gum (called hydroxyalkyl guars), containing per molecule of the order of 0.01 to 5, preferably of the order of 0.05 to 0.5 oxyalkylene, preferably oxyethylene and/or oxypropylene unit(s); they can be obtained by reaction of natural guar with an alkylene oxide (ethylene and/or propylene oxide).

The gel (gel G1) according to the invention may include very particularly as hydrocolloid a mixture (M) containing:

a succinoglycan polysaccharide, and a hydroxyalkyl guar containing of the order of 0.01 to 5, preferably of the order of 0.05 to 0.5 oxyethylene and/or oxypropylene unit(s), according to a hydroxyalkyl guar/succinoglycan weight ratio of the order of 20/80 to 95/5, preferably of the order of 50/50 to 90/10.

The mixture (M) can be prepared by dry mixing of powders of hydrocolloid polysaccharide obtained by bacterial fermentation (BPS) and of hydrocolloid polymer of natural origin (NP) by any method known to a person skilled in the art.

The invention also relates to the process of preparation of the gel according to the invention, which consists in mixing its various constituents, the neutralizing agent (NA) and the "multichain" surfactant (MCSA) being each introduced separately into the apolar medium (ApoM), the neutralizing agent (NA) being preferably introduced after the "multichain" surfactant (MCSA).

A preferred embodiment consists in introducing, with mechanical stirring, the "multichain" surfactant (MCSA) into the apolar medium (ApoM) heated to a temperature of the order of 15° to 50° C., generally of the order of 25° to 35° C., followed by the optional emulsifier, the neutralizing agent (NA) and the optional fillers.

When the gel has the composition of the gel G1, it can be prepared by introducing the "multichain" surface-active agent (MCSA), then the neutralizing agent (NA) and finally the hydrocolloid into the apolar medium (ApoM) with mechanical stirring.

Another subject of the present invention is a process for gelling an apolar medium (ApoM), the said process being characterized in that the following are introduced into the said apolar medium:

at least one "multichain" liquid surface-active agent in acidic form (MCSA) which is soluble or dispersible in the said apolar medium at least one agent for neutralizing (NA) the said "multichain" surface-active agent, present in a quantity corresponding to approximately 2 to 30 times, preferably 4 to 20 times the quantity stoichiometrically necessary for the neutralization of the said "multichain" surface-active agent in acidic form (MCSA)

of the order of 0.2 to 5, preferably of the order of 0.3 to 3 molecules of water per molecule of "multichain" liquid surface-active agent in acidic form (MCSA), the water being introduced at least partially through the intermediacy of the said "multichain" surface-active agent in acidic form (MCSA) and/or through the intermediacy of the said neutralizing agent (NA)

optionally at least one emulsifying agent capable of emulsifying the gel obtained in water or in an aqueous medium and optionally at least one solid filler which is soluble or insoluble in the apolar medium (ApoM).

The nature and the respective quantities of the various constituents as a function of the intended utilization of the gel to be obtained, and the operating conditions, have already been mentioned above.

Furthermore the invention relates to the use of the gel (gel G1) for the preparation of a water-based drilling fluid and in particular for the preparation of a water-based drilling fluid for the manufacture of moulded walls.

The process for the preparation of such drilling fluids consists in diluting the gel (gel G1) in water.

In general, in the case of this process of preparation, quantities of gel and water are diluted in such a way that the final drilling fluid includes 0.01 to 3 part(s) by weight of hydrocolloid capable of thickening aqueous media, introduced through the intermediacy of the gel, per 100 parts of water. The drilling fluid preferably, includes of the order of 0.05 to 1.5 parts by weight of hydrocolloid per 100 parts of water.

The use of the gel (gel G1) according to the invention for the preparation of water-based drilling fluids has a number of advantages.

First of all, the drilling fluids obtained include only water and small quantities of the gel (gel G1). The fact that small quantities of the gel (gel G1) are employed allows, after use, the drilling fluid present in the soil earth to be disposed in an unclassified dump. In fact, since the gel (gel G1) is rapidly biodegradable, storage of the spoils does not require any particular condition.

Next, the drilling fluids obtained exhibit a high water retention, and this prevents seepages of water in the terrain when a cutting is being drilled, especially in the case of the construction of moulded walls. The drilling fluids employed generally exhibit a filtrate at 30 min ($V_{30}$) of not more than 30 ml, preferably of not more than 25 ml, still more preferably of not more than 20 ml, the method for measuring the filtrate being that given in the examples.

The fluids obtained also have rheological properties which are suitable for their use for the manufacture of moulded walls. In particular, they have a pseudoplastic behaviour such that they can be easily pumped without it being necessary to use highly shearing means of agitation.

In general, the drilling fluids obtained from the gel (gel G1) according to the invention exhibit a Fann plastic viscosity ($V_p$) of between 5 and 15 mPa s, preferably between 5 and 10 mPa s. They also exhibit a Marsh viscosity ($V_M$) of between 30 and 140 s, preferably between 30 and 100, still more preferably between 35 and 50 s. They also exhibit a yield value (YV) of between 2 and 10 Pa. These various viscosities are measured according to the tests described in the examples.

Finally, the drilling fluids obtained from the gel (gel G1) maintain their properties after coming into contact with soil and the $Ca^{2+}$ ions of the concrete. Thus, after separation of the spoils from the drilling fluid a considerable part of this fluid can be recycled. This is a considerable advantage when compared with the known fluids of the prior art, based in general on bentonite, which are not recyclable: in fact, they lose their rheological properties after coming into contact with the soluble ions which may be present in the soil or with the $Ca^{2+}$ ions of the concrete.

The invention finally relates to the use of the gel (gel G1) in combination with a surface-active agent (SA) as a precursor system for a drilling fluid in foam form, for drilling tunnels with the aid of a tunnelling machine.

The invention therefore also relates to a precursor system for a drilling fluid in foam form including the gel (gel G1) according to the invention and a surface-active agent (SA).

The surface-active agent (SA) may be chosen from any type of water-soluble surface-active agent which is compatible with the hydrocolloids capable of thickening the aqueous media forming part of the gel (gel G1). These surface-active agents must make it possible to forms a foam and must be chemically and thermally stable in the storage conditions. They may involve a cationic, anionic, ionic or amphoteric surface-active agent.

The surface-active agent (SA) of the foam precursor system may, in particular, be chosen from:
alkyl sulfates of formula $ROSO_3M$ where R denotes a $C_5$–$C_{24}$, preferably $C_{10}$–$C_{18}$ alkyl or hydroxyalkyl radical, M denoting a hydrogen atom or an alkali metal (sodium, potassium, lithium) or substituted or unsubstituted ammonium cation (methyl-, dimethyl-, trimethyl-, tetramethylammonium, dimethylpiperidinium etc.) or one derived from an alkanolamine (monoethanolamine, diethanolamine, triethanolamine, monoisopropanolamine, etc.);

betaines, alkylbetaines, alkyldimethylbetaines, alkylamidobetaines, alkyltrimethylsulfobetaines;

mixtures of alkylamidobetaines and of sodium alkylsulfosuccinates where the alkyl radical is $C_4$–$C_{18}$;

alkyl ether sulfates $RO(CH_2CHR_1O)_nSO_3M$ where n is between 0.5 and 30, preferably between 0.5 and 10 and where $R_1$ is a $C_4$–$C_{18}$, preferably $C_{12}$–$C_{15}$ alkyl group and containing, on average, from 0.5 to 30 units, preferably from 0.5 to 10 oxyethylene and/or oxypropylene units, M denoting a hydrogen atom or an alkali metal (sodium, potassium, lithium) or substituted or unsubstituted ammonium cation (methyl-, dimethyl-, trimethyl-, tetramethylammonium, dimethylpiperidinium, etc.) or one derived from an alkanolamine (monoethanolamine, diethanolamine, triethanolamine, monoisopropanolamine, etc.);

alpha-olefin sulfonates;

alkylpolyglycosides of formula $R(OCH_2CH_2)_n(G)_m$, where R is a $C_8$–$C_{24}$ saturated or unsaturated, linear or branched hydrocarbon radical, G is a $C_5$–$C_6$ reducing sugar such as galactose, glucose or fructose, n being between 0 and 20 and m between 1 and 10;

alkylamphomonoacetates and alkylamphodiacetates such as especially the sodium cocoamphoacetate marketed under the names Mirapon Excel® and Miranol Ultra® by Rhone-Poulenc.

The respective quantities of surface-active agent (SA) and of gel of the precursor system of drilling fluid in foam form may be very variable as a function of the application of the precursor system. The surfactant (SA) content may thus be between 1 and 2000% by weight relative to the weight of the gel (gel G1).

The precursor system of drilling fluid in foam form according to the invention may additionally include at least one solid filler other than the hydrocolloids which are capable of thickening aqueous media, such as:

natural silica (sand, diatoms, etc.) or synthetic silica (from precipitation etc.), calcium carbonate, magnesium carbonate, metal oxides such as iron oxide (haematite, magnetite, etc.), natural (ochre, etc.) or synthetic pigments, foam-regulating agents such as aluminium stearate, hydrophobic silica, ethylenebisstearamide, natural, slaked or hydroic lime, etc.

gypsum (anhydrite, semihydrate), active substances like plant-protection compounds, water-soluble basic compounds such as sodium metasilicates, polysilicates, clays (kaolin, smectite, illite), talcs, mica, etc.

These solid fillers may represent not more than 50% by weight of the precursor system of drilling fluid in foam form, preferably not more than 20%, still more preferably not more than 15%.

The particle size is generally between 0.1 $\mu$m and 1 mm, preferably between 0.2 $\mu$m and 200 $\mu$m.

These fillers may be introduced entirely or partly into the precursor system by means of the gel (gel G1). In fact, the gel forming part of the composition of the precursor may include solid fillers.

In general, when a low proportion of solid fillers is introduced into the precursor system, the said fillers are introduced entirely by means of the gel (gel G1).

The solid fillers may also be introduced separately from the gel (gel G1).

The invention also relates to a process for the preparation of drilling fluid in foam form, which consists in diluting the precursor system defined above in water and in agitating. This agitation is conventionally produced by introducing a compressed gas such as air or nitrogen into the precursor system of drilling fluid in foam form, diluted in water.

The precursor system is diluted in water in such a way that the final quantity of the surface-active agent (SA) of the precursor system in water is generally between 0.05 and 25% by weight relative to the water, preferably between 0.05 and 15%, still more preferably between 0.2 and 1.5%.

The foam is preferably created in such a way that the expansion coefficient K, measured at atmospheric pressure, is between 5 and 10, the coefficient K being determined by the following relationship:

$$K = Vm/Va$$

where Vm is the volume of the foam after activation of the precursor system in solution, and Va is the volume of the precursor system in solution before activation.

The foam may be created conventionally in a foam generator. For example, when foam is employed for drilling tunnels with the aid of a tunnelling machine, this foam may be injected by suitable means, in front of the cutter disk and/or into the confinement chamber, where it mixes with the soil.

Finally, the invention relates to the use of the drilling fluid in foam form obtained with the aid of the precursor system for the excavation of tunnels, for example with the aid of a tunnelling machine, especially by means of a driving shield such as an earth-pressure shield.

The composition of the precursor system of drilling fluid in foam form (in particular the respective quantities of the surface-active agent (SA) and of the gel) varies as a function of the nature of the terrain in which the tunnel is excavated. A person skilled in the art knows how to adapt the quantities of surface-active agent (SA) and of gel as a function of the terrain to be dug.

The drilling fluid in foam form obtained with the aid of the precursor system exhibits a number of advantages in this application.

It allows the friction of the cutting disk on the cutting face to be considerably reduced.

It has a good stability although it is subjected to pressures which are higher than the atmospheric pressure and to shear stresses prevailing on the front face of the cutting cylinder, in the confinement chamber and at the endless screw of the tunnelling machine.

This fluid in foam form is also easily pumpable as a result of these plastic properties.

Finally, it makes it possible to improve the fluidity of clay-based soils.

The following examples illustrate the invention without, however, limiting its scope.

EXAMPLES

General procedure for preparing the gel

The apolar medium (ApoM) is placed in a 1-liter container.

The "multichain" agent (MCSA) is introduced into it at ambient temperature, with stirring with the aid of a Rayneri® deflocculating paddle marketed by Rayneri, rotating at 400 revolutions/minute; stirring is continued for 5 minutes more.

The neutralizing agent (NA) is introduced next and stirring is applied for 5 minutes.

The optional hydrocolloid is finally added.

After stirring for 5 minutes the mixture is allowed to stand for approximately 2 hours.

Example 1 gel (G1-1) for water-based drilling fluid

The following gel (G1-1) is prepared according to the above procedure:

TABLE 1

| Ingredients | Parts by weight | % by weight |
| --- | --- | --- |
| Rapeseed oil | 335 | 67 |
| Lubrhophos LL550 ®* | 10 | 2 |
| Aminomethylpropanol | 5 | 1 |
| Rhodopol 23 ®** | 150 | 30 |

Figure 1:
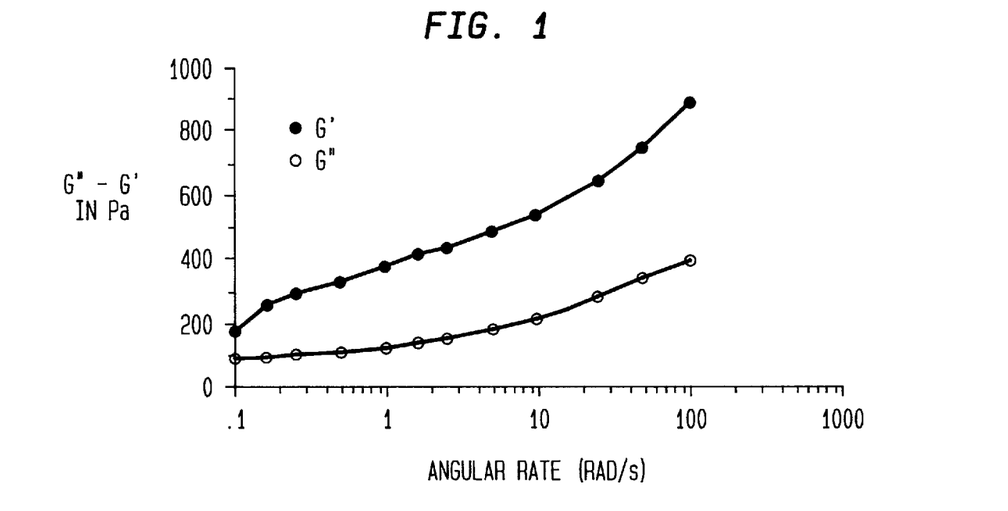
FIG. 1 shows the variation in conservation and deformation modulus as a function of the angular rate of deformation.

*"multichain" surfactant based on $C_8$–$C_{14}$ ethoxylated phosphate diester containing 5.5 oxyethylene units, containing water in a quantity of less than 2% by weight, marketed by Rhône-Poulenc The gel (G1-1) obtained is a "flexible" gel. The curve given in FIG. 1 shows the variation in the conservation modulus G' and of the deformation modulus G" as a function of the angular rate of deformation expressed in radian/s.

This gel (G1-1) is next dispersed in water, in a quantity making it possible to obtain a diluted medium which has a xanthan gum concentration of 0.5% by weight.

Figure 2:
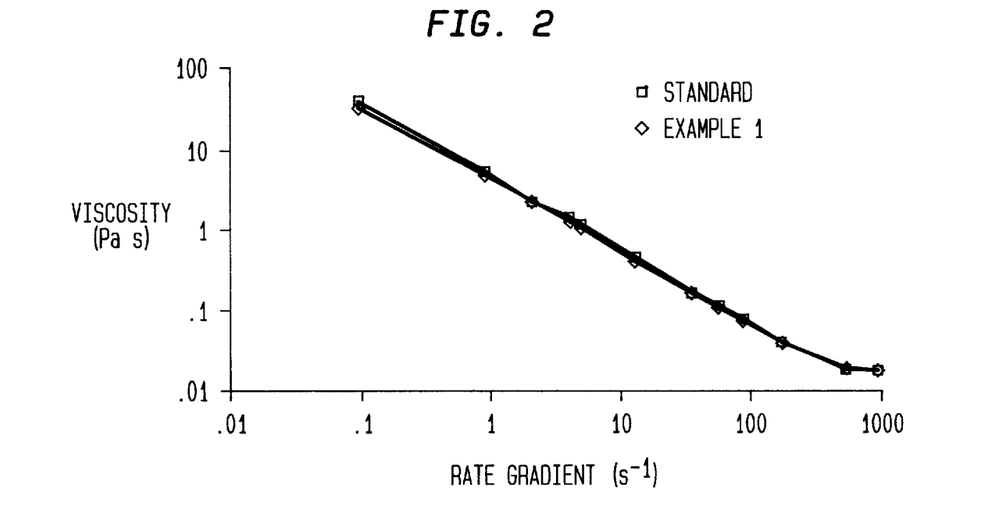
FIG. 2 shows the variation of the dynamic viscosity of the medium as a function of the rate gradient.

FIG. 2 shows that the variation in the dynamic viscosity of the medium obtained as a function of the rate gradient, measured with the aid of the Rheomat 115® marketed by Contraves, is in practice similar to that of a solution of xanthan gum at a concentration of 0.5% in water.

The dispersion obtained is therefore pumpable.

Example 2 gel (G1-2) for cosmetic composition

The following gel (G1-2) is prepared according to the procedure defined above:

TABLE 2

| Ingredients | Parts by weight | % by weight |
| --- | --- | --- |
| Olive oil | 442.5 | 88.5 |
| Rhodafac PC 100 ®* | 30 | 6 |
| Aminomethylpropanol | 27.5 | 5.5 |

*"multichain" surfactant based on a mixture of ethoxylated mono- and dilauryl phosphate esters containing water in a quantity of less than 2% by weight, marketed by Rhône-Poulenc The gel obtained is "hard"

Example 3 comparative

The following composition is prepared according to the procedure defined above:

TABLE 3c

| Ingredients | % by weight |
| --- | --- |
| Rapeseed oil | 87 |
| Dodecylbenzenesulphonic acid | 5 |
| Aminomethylpropanol | 8 |

The use of dodecylbenzenesulphonic acid, which is a non-multichain surfactant, in the composition does not make it possible to obtain a gel in apolar medium. The composition remains fluid.

Example 4 rheological properties of a drilling fluid prepared with the aid of a gel (G1-3) according to the invention, including hydrocolloids in the form of a mixture (M).

Preparation of a mixture (M)

A mixture of hydroxypropyl guar containing 0.4 oxypropylene units per molecule (Jaguar HP8® from Rhone- Poulenc) exhibiting a pseudoplasticity value in solution at a concentration of 0.3% by weight in water of hardness 22TH (324 mg/l of $CaCl_2.2H_2O$) of 0.94 and of Rheozan® (from Rhone-Poulenc) exhibiting a pseudoplasticityvalue in solution at a concentration of 0.1% by weight in water of hardness 22TH (324 mg/l of $CaCl_2.2H_2O$) of 0.36 is mixed in a weight ratio of 80/20.

A gel (G1-3) is prepared as in Example 1, except that the Rhodopol 23® is replaced with the mixture (M).

The gel (G1-3) is dispersed in water, in a quantity which makes it possible to obtain a diluted medium exhibiting a mixture (M) concentration of 1% by weight. The properties of the drilling fluid obtained are studied at different pH values of 4.5, 9.6 and 13 and in the presence or absence of cement in concentrations of 1 or 5% by weight.

The gel (G1-3) and the cement are added to the 22TH water with stirring with the aid of an IKA stirrer at 1500 rev/min.

The measurements at different pH values make it possible to express the behaviour of the drilling fluid in contact with more or less acidic terrains. The adjustment of the pH is made immediately after the dispersion of the gel (G1-3) in water, and the solution is then left at rest for 1 hour before the optional addition of cement (Portland CPA 55).

The adjustment of the pH values is made with the aid of 10% acetic acid in the case of the pH of 4.5 and with the aid of 10% sodium hydroxide in the case of the pH of 13. The pH of 9.6 corresponds to the natural pH of the gel (G1-3) including the mixture (M).

Measurements carried out

In the case of solutions of different concentrations the values of plastic viscosity ($V_p$), of yield value (YV) and of Marsh viscosity ($V_M$) are measured at 0 h, 2 h or 24 h after preparation of the different fluids. The measurements are carried out according to the following tests.

a. Test for the plastic viscosity ($V_p$) and yield value ($Y_v$):

400 g of a water-based fluid are prepared by diluting the gel (G1-3) in water: the gel is hydrated in 22TH water with the aid of an IKA stirrer, the deflocculating paddle rotating at a rate of 400 rev/min during the introduction of the gel and then at 800 rev/min for 15 min, and then the viscosity of the solution is measured with the aid of a Fann viscometer at 300 and 600 rev/min;

this gives:

the plastic viscosity: $V_p = L_{600} - L_{300}$ in MPa s, and the yield value $YV = L_{600}/2 - V_p$ in Pa.

b. Test for the Marsh viscosity ($V_M$):

1000 g of a water-based fluid are prepared by diluting the gel (G1-3) in water: the mixture (M) is hydrated in 22TH water with the aid of an IKA stirrer, the deflocculating paddle rotating at a rate of 800 rev/min during the introduction of the gel and then for 15 min, the flow time in seconds of 946 cc of solution is measured with the aid of a Marsh viscometer.

The results are listed together in Table 3.

TABLE 3

| Formulation | Initial pH of the gel(G1-3) | Age | $V_p$ | YV | $V_M$ |
|---|---|---|---|---|---|
| G1-3 | 9.6 | 2 h | 7 | 5 | 44 |
|  |  | 24 h | 7 | 5 | 46 |
| G1-3 | 4.5 | 2 h | 7 | 5 | 47 |
|  |  | 24 h | 7 | 5 | 47 |
| G1-3 | 13 | 2 h | 6 | 3 | 40 |
|  |  | 24 h | 6 | 3.5 | 40 |

TABLE 3-continued

| Formulation | Initial pH of the gel(G1-3) | Age | $V_p$ | YV | $V_M$ |
|---|---|---|---|---|---|
| G1-3 | 9.6 | 0 h | 7 | 4 | 42 |
| 1% cement |  | 24 h | 7 | 4 | 42 |
| G1-3 | 4.5 | 0 h | 8 | 4 | 42 |
| 1% cement |  | 24 h | 7 | 3.5 | 43 |
| G1-3 | 13 | 0 h | 6 | 1.5 | 37 |
| 1% cement |  | 24 h | 5 | 2 | 42 |
| G1-3 | 9.6 | 0 h | 7 | 4 | 38 |
| 5% cement |  | 24 h | 6 | 3 | 30 |
| G1-3 | 4.5 | 0 h | 8 | 4 | 40 |
| 5% cement |  | 24 h | 6 | 4.5 | 32 |
| G1-3 | 13 | 0 h | 7 | 3.5 | 40 |
| 5% cement |  | 24 h | 6 | 4 | 38 |

It is found that the values of the plastic viscosity ($V_p$), of the Marsh viscosity ($V_M$) and of the yield value (YV) are not greatly affected by the presence of cement in concentrations of 1 or 5% by weight.

The value of the filtrates was also measured in order to evaluate the ability of the fluid to retain water. To do this, the fluids are filtered after contamination by cement with a low-temperature pressure filter (Fann model 12 BL 2) and the volume of filtrate is measured for t=1 min, 4 min, 7 min 30 s and 30 min: $V_1$, $V_4$, $V_{7.3}$ and $V_{30}$.

The results are listed together in Table 4.

TABLE 4

| Formulation | Initial pH of the gel (G1-3) | Age | $V_1$ | $V_4$ | $V_{7.3}$ | $V_{30}$ |
|---|---|---|---|---|---|---|
| G1-3 | 4.5 | 2 h | 7.5 | 10 | 11.5 | 18 |
| G1-3 | 9.6 | 0 h | 4 | 7 | 8.5 | 15 |
| 1% cement |  | 24 h | 6 | 8.1 | 9.8 | 16.4 |
| G1-3 | 4.5 | 0 h | 4 | 7 | 8.2 | 14.8 |
| 1% cement |  | 24 h | 4.6 | 6.9 | 8.5 | 16 |
| G1-3 | 13 | 0 h | 2.4 | 4 | 5.6 | 12.4 |
| 1% cement |  | 24 h | 1 | 1.6 | 4.4 | 11.8 |
| G1-3 | 9.6 | 0 h | 6 | 12 | 15 | 24 |
| 5% cement |  | 24 h | 3 | 4.8 | 6.2 | 14 |
| G1-3 | 4.5 | 0 h | 5 | 11 | 14.6 | 24.8 |
| 5% cement |  | 24 h | 5 | 7 | 8.8 | 17 |
| G1-3 | 13 | 0 h | 5 | 8.5 | 11 | 19.8 |
| 5% cement |  | 24 h | 13 | 26 | 31 | 42 |

It is noted that the filtrate values remain low even in the presence of cement. The drilling fluid maintains its property of water retention after use.

Example 5 comparative—bentonite

Bentonite-based drilling fluids are produced and are subjected to the same tests as in Example 3. The results are listed together in Tables 5 and 6.

The natural pH of the bentonite-based drilling fluid is 10.7.

TABLE 5

| Formulation | Initial pH of the drilling fluid | Age | $V_p$ | YV | $V_M$ |
|---|---|---|---|---|---|
| bentonite | 10.7 | 2 h | 7 | 5 | 41 |
| bentonite | 4.5 | 2 h | 5 | 0 | 33 |
| bentonite | 13 | 2 h | 5 | 54 | gel |
| bentonite | 10.7 | 0 h | 7 | 24 | 58 |
| 1% cement |  | 24 h | gel | gel | gel |

TABLE 5-continued

| Formulation | Initial pH of the drilling fluid | Age | $V_p$ | YV | $V_M$ |
|---|---|---|---|---|---|
| bentonite 1% cement | 4.5 | 0 h | 7 | 7 | 36 |
| | | 24 h | 8 | 6.5 | gel |
| bentonite 1% cement | 13 | 0 h | 11 | 6.5 | 38 |
| | | 24 h | 14 | 9 | gel |
| bentonite 5% cement | 10.7 | 0 h | 17 | 15 | 45 |
| | | 24 h | gel | gel | gel |
| bentonite 5% cement | 4.5 | 0 h | 7 | 5.5 | 36 |
| bentonite 5% cement | 13 | 0 h | 25 | 15 | 240 |

It is noted that bentonite contaminated with cement gels after 24 h. This gel is not pumpable and can no longer be employed as a drilling fluid for the manufacture of moulded walls.

TABLE 6

| Formulation | pH | Age | $V_1$ | $V_4$ | $V_{7.3}$ | $V_{30}$ |
|---|---|---|---|---|---|---|
| bentonite | 4.5 | 2 h | 3 | 7 | 9 | 17 |
| bentonite 1% cement | 10.7 | 0 h | 16 | 33.5 | 46.8 | 99.8 |
| | | 24 h | gel | gel | gel | gel |
| bentonite 1% cement | 4.5 | 0 h | 29.5 | 59.2 | 85.4 | gel |
| | | 24 h | 38 | 76 | 106 | gel |
| bentonite 1% cement | 13 | 0 h | 11 | 24 | 30.2 | 79.7 |
| | | 24 h | 24 | 49 | 67 | gel |
| bentonite 5% cement | 10.7 | 0 h | 26.3 | 52.4 | 74 | gel |
| | | 24 h | gel | gel | gel | gel |
| bentonite 5% cement | 4.5 | 0 h | 40 | 81 | 114 | gel |
| bentonite 5% cement | 13 | 0 h | 17 | 34 | 47 | 102 |

It is found that, as soon as bentonite is in contact with $Ca^{2+}$ ions, the filtrate values increase considerably: bentonite, which exhibited good water retention properties in the absence of cement ($V_{30}$<20 ml) no longer provides this function after a first use in the presence of cement.

Example 6

Precursor system of drilling fluid in foam form, use in sand-gravel mixture

The following are introduced into water:

the gel (G1-1) of Example 1 in a proportion of 1% by weight relative to the weight of water, and Rhodapex AB-20 from Rhone-Poulenc as surface-active agent (SA) in a proportion of 0.5% by weight relative to the weight of water. Rhodapex AB-20 is an ammonium alkyl ether sulphate.

This mixture is then stirred with the aid of a bladed stirrer and the composition obtained is left to stand for a few minutes.

The composition is next injected into a foam generator and is mixed with a sandy-gravelly soil saturated with 15% of water. The composition is introduced in a proportion of 2% by weight relative to the weight of the soil and of the water in the said soil.

In order to control the fluidity of the soil mixed with the foam, a measurement of the soil is carried out using the Abrams cone: the result is 15 cm. This measurement expresses the plastic behaviour of the soil containing the foaming agent. It is found, furthermore, that the mixture does not settle.

This soil is therefore easily pumpable and removable, in contrast with a sandy soil without addition of foam, which exhibits a rapid settlement and no plastic behaviour.

It is also found that the soil does not adhere to steels: the foam therefore makes it possible to reduce friction with the toothed wheel.

Example 7

Precursor system of drilling fluid in foam form, use in sandy environment

The following are introduced into water:

the gel (G1-1) of Example 1 in a proportion of 1% by weight relative to the weight of water, and Rhodapex AB-20 as surface-active agent (SA) in a proportion of 0.8% by weight relative to the weight of water, and this mixture is then stirred with the aid of a bladed stirrer and the composition obtained is allowed to stand for a few minutes.

The composition is next injected into a foam generator and is mixed with a sandy soil exhibiting a strong particle size discontinuity between 0.1 and 0.3 mm and a water content of 16%. The composition is introduced in a proportion of 3% by weight relative to the weight of the soil and of the water in the said soil.

In order to control the fluidity of the soil mixed with the foam, a measurement of the soil is carried out using the Abrams cone; the result is 15 cm. This measurement expresses the plastic behaviour of the soil containing the foaming agent. It is found, furthermore, that the mixture does not settle.

This soil is therefore easily pumpable and removable, in contrast with a sandy soil without addition of foam, which exhibits a rapid settling and no plastic behaviour.

It is also noted that the soil does not adhere to steels: the foam therefore makes it possible to reduce friction with the toothed wheel.

Example 8

Precursor system of drilling fluid in foam form, use in clayey environment

The following are introduced into water:

the gel (G1-1) in a proportion of 0.1% by weight relative to the weight of water, and Rhodapex AB-20 in a proportion of 1.5% by weight relative to the weight of water, and this mixture is then stirred with the aid of a bladed stirrer and the composition obtained is left to stand for a few minutes.

The composition is next injected into a foam generator and is mixed with an alluvial soil exhibiting a clay content of between 15 and 18% and a water content of 15%. The composition is introduced in a proportion of 10% by weight relative to the weight of the soil.

In order to control the fluidity of the soil mixed with the foam, a measurement of the soil is carried out using the Abrams cone: the result is 15 cm. This measurement expresses the plastic behaviour of the soil containing the foam. It is found, furthermore, that the mixture does not settle.

This soil is therefore easily pumpable and removable, in contrast with a sandy soil without addition of foam, which exhibits rapid settling and no plastic behaviour.

It is also found that the soil does not adhere to steels: the foam therefore makes it possible to reduce friction with the toothed wheel.

What is claimed is:

1. A gel of an apolar medium comprising:
   (1) an apolar medium.
   (2) a multichain liquid surface-active agent in acidic form which is soluble or dispersible in the said apolar medium selected from the group consisting of phosphate diesters of alkoxylated alcohols containing from about 2 to about 20 oxyalkylene units containing from about 2 to about 4 carbon atoms, the alcohol being a $C_6$–$C_{30}$ linear or branched, saturated or unsaturated aliphatic alcohol, phosphate diesters of alkoxylated alkylphenols containing from about 2 to about 20 oxyalkylene units containing from about 2 to about 4 carbon atoms, the alkylphenol having a $C_6$–$C_{30}$ all group, and mixtures thereof,
   (3) a neutralizing agent for said multichain surface-active agent, present in a quantity corresponding to about 2 to about 30 times the quantity stoichiometrically necessary for the neutralization of the said multichain surface-active agent, and
   (4) from about 0.2 to about 5 parts by mole of water per mole of multichain liquid surface-active agent, the water being introduced at least partly through the intermediacy of the said multichain surface-active agent or through the intermediacy of said neutralizing agent.

2. The gel according to claim 1, further comprising:
   (5) one emulsifying agent capable of emulsifying said gel in water or in an aqueous medium.

3. The gel according to claim 1, further comprising:
   (6) one solid filler which is soluble or insoluble in the apolar medium.

4. The gel according to claim 1, wherein component (1) is selected from the group consisting of triglycerides of saturated or unsaturated fatty acids containing at least 12 carbon atoms, aromatic petroleum cuts, terpinic compounds, mixtures of dimethyl, dipropyl, diisobutyl and dibutyl succinate/adipate/glutarate diesters, aliphatic hydrocarbons containing at least 6 carbon atoms, aromatic solvents, chlorinated solvents, essential oils, and mixtures thereof.

5. The gel according to claim 1, wherein component (3) is selected from the group consisting of primary, secondary amines, tertiary amines and alkanolamines.

6. The gel according to claim 5, wherein component (3) is selected from the group consisting of triethanolamine, aminomethylpropanol, cocoamine and butylamine.

7. The gel according to 3, wherein component (5) is selected from the group consisting of ethoxylated tristyrylphenols, ethoxylated tristyrylphenol sulfates, propoxylated tristyrylphenol sulfates, ethoxylated tristyrylphenol phosphates, propoxylated tristyrylphenol phosphates, ethoxylated fatty acids, propoxylated fatty acids, ethoxylated alcohols, propoxylated alcohols, ethoxylated/propoxylated block copolymers and sodium dodecylbenzenesulfonate.

8. The gel according to claim 3, wherein component (6) is selected from the group consisting of silica, calcium carbonate, pigments, hydrocolloids capable of thickening an aqueous media, foam suppressors, sodium metasilicates, clays, titanium oxide, zinc oxide and the possible mixtures thereof.

9. The gel according to claim 8, wherein component (6) comprises hydrocolloids capable of thickening an aqueous media which are selected from the group consisting of:
   polysaccharides obtained by bacterial fermentation,
   galactomannans,
   carrageenans,
   alginates,
   semisynthetic cellulose derivatives,
   alkali metal polyacrylates,
   polyvinyl alcohols,
   polyethylene glycols, and
   polyvinylpyrrolidones.

10. The gel according to claim 1, wherein the quantity of component (2) is about 0.5 to about 10%, by weight relative to the said gel.

11. The gel according to claim 1, wherein the quantity of component (2) is about 1 to about 3% by weight relative to the weight of the said gel, wherein the molar ratio of component (3) of to component (2) is about 5 to about 10 times the stoichiometric neutralization ratio, and wherein the quantity of water is about 0.01 to about 0.1% by weight relative to the weight of the said gel.

12. The gel according to claim 1, wherein the quantity of multichain surfactant is of about 5 to about 10% by weight relative to the weight of the said gel, wherein the molar ratio of component (3) to component (2) is about 5 to about 10 times the stoichiometric neutralization ratio, and wherein the quantity of water is about 0.05 to about 0.5% by weight relative to the weight of the said gel.

13. The gel according to claim 9, wherein the hydrocolloid capable of thickening an aqueous media is selected from the group consisting of xanthan gum, polysuccinoglycans, rhamsan, wellan, and gellan.

14. The gel according to claim 9, wherein the hydrocolloid capable of thickening an aqueous media is a mixture comprising:
   (i) a hydrocolloid polysaccharide obtained by bacterial fermentation stable in the presence of $Ca^{2+}$ ions and at a pH higher than about 10 and exhibiting a pseudoplasticity value lower than or equal to about 0.5 at a concentration of about 0.1% by weight in distilled water, and
   (ii) a hydrocolloid polymer of natural origin, stable in the presence of cement and of $Ca^{2+}$ ions at a pH higher than 10 and exhibiting a pseudoplasticity value higher than or equal to 0.6 at a concentration of 0.3% by weight in distilled water according to a component i component ii weight ratio of the order of 20/80 to 95/5.

15. The gel according to claim 14 wherein the hydrocolloid polymer of natural origin is a semisynthetic cellulose derivative or an alkoxylated derivative of guar gum containing from about 0.01 to about 5 oxyalkylene unit(s) per molecule.

16. The gel according to claim 14 wherein the hydrocolloid polymer of natural origin is selected from the group consisting of hydroxymethyl cellulose, hydroxyethyl cellulose, hydroxymethyl propyl cellulose, a hydroxypropyl cellulose, carboxymethyl cellulose or hydroxyalkyl guar containing from about 0.01 to about 5 oxyethylene and/or oxypropylene unit(s) per molecule.

17. The gel according to claim 14 wherein the mixture comprises:
   a succinoglycan polysaccharide
   and a hydroxyalkyl guar containing from about 0.01 to about 5 oxyethylene and/or oxypropylene unit(s) having a hydroxyalkyl guar/succinoglycan weight ratio of about 20/80 to about 95/5.

18. A water-based drilling fluid or molded wall composition comprising:

(1) an apolar medium having the following parameters: δP of Keesom interactions lower than 10 $(J/cm^3)^{1/2}$, δH of hydrogen bonds lower than 10 $(J/cm^3)^{1/2}$, and δD of London interactions higher than 15 $(J/cm^3)^{1/2}$;

(2) about 0.5 to about 6.0 parts by weight of a multichain liquid surface-active agent in acidic form which is soluble or dispersible in said apolar medium which are phosphate diesters of alkoxylated alcohols containing from 2 to 20 oxyethylene units, or phosphate diesters of alkoxylated alkylphenols containing from 2 to 20 oxyethylene units;

(3) a neutralizing agent for said multichain surface-active agent, present in a quantity corresponding to about 2 to about 30 times the quantity stoichiometrically necessary for the neutralization of said multichain surface active agent and which are primary, secondary or tertiary amines or alkanolamines;

(4) from about 0.2 to about 5 parts by mole of water per mole of multichain liquid surface-active agent; and about 10 to about 50 parts by weight of one or more hydrocolloids which are polysaccharides, galactomannans, carrageenans, alginates carboxymethyl celluloses, methyl celluloses, hydroxypropyl celluloses, hydroxyethylcelluloses, alkali metal polyacrylates, polyvinyl alcohols, polyethylene glycols or polyvinylpyrrolidones: wherein the total weight of said composition is 100 parts.

19. The composition according to claim 18 comprising a water-based drilling fluid.

20. The drilling fluid composition according to claim 19 wherein said composition is diluted in water whereby after said dilution the fluid includes 0.01 to 3 part by weight of hydrocolloid per 100 parts of water capable of thickening an aqueous media.

21. The drilling fluid composition according to claim 20, further comprising a surface-active agent, said composition being in the form of a foam precursor.

22. The composition according to claim 21 wherein the surface-active agent is selected from the group consisting of:

alkyl sulfates of formula $ROSO_3M$ where R denotes a $C_5$–$C_{24}$ alkyl or hydroxyalkyl group, M denotes a hydrogen atom, an alkali metal and a substituted or unsubstituted ammonium cation;

alkylbetaines, alkyldimethylbetaines, alkylamidobetaines, alkyltrimethylsulphobetaines;

mixtures of alkylamidobetaines and of sodium alkylsulfosuccinates wherein the alkyl group is $C_4$–$C_{18}$;

alpha-olefin sulfonates;

alkylpolyglycosides of formula $R_3(OCH_2CH_2)_s(G)_p$, where $R_3$ is a $C_8$–$C_{24}$ saturated or unsaturated, linear or branched hydrocarbon radical, G is a $C_5$–$C_6$ reducing sugar being galactose, glucose or fructose, s is between 0 and about 20 and p is between 1 and about 10; and alkylamphomonoacetates, alkylamphodiacetates.

23. The composition according to claim 21 wherein the surface-active agent content is between about 1 and 2000% by weight relative to the weight of said composition.

24. The composition according to claim 21, further comprising a solid filler selected from the group consisting of:

natural or synthetic silica, calcium carbonate, magnesium carbonate, metal oxides, natural or synthetic pigments, foam-regulating agents, natural, slaked or hydroic lime, gypsum, sodium metasilicates, polysilicates, clays, talcs and mica.

25. The composition according to claim 24 wherein the quantity of solid filler represents not more than 50% by weight of said composition.

26. The composition according to claim 21 which is distributed in water such that the final quantity of surface-active agent is between about 0.05 and about 25% by weight of said water.

* * * * *